United States Patent

Brumer et al.

(10) Patent No.: US 8,896,423 B2
(45) Date of Patent: *Nov. 25, 2014

(54) PHYSIOLOGICAL SENSOR SYSTEM WITH AUTOMATIC AUTHENTICATION AND VALIDATION BY MEANS OF A RADIO FREQUENCY IDENTIFICATION PROTOCOL WITH AN INTEGRATED RFID INTERROGATOR SYSTEM

(71) Applicant: Covidien LP, Mansfield, MA (US)

(72) Inventors: Rebecca Brumer, Arlington, VA (US); Nassib G. Chamoun, Needham, MA (US); Rafael M. Cordero, Bedford, MA (US); Marc Davidson, Andover, MA (US); James P. Kiely, Belmont, MA (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/867,007

(22) Filed: Apr. 19, 2013

(65) Prior Publication Data

US 2013/0234830 A1  Sep. 12, 2013

Related U.S. Application Data

(63) Continuation of application No. 13/315,486, filed on Dec. 9, 2011, now Pat. No. 8,427,321, which is a continuation of application No. 11/871,585, filed on Oct. 12, 2007, now Pat. No. 8,077,039.

(60) Provisional application No. 60/851,437, filed on Oct. 13, 2006.

(51) Int. Cl.
*G08B 13/14* (2006.01)
(Continued)

(52) U.S. Cl.
CPC .............. *G08C 17/02* (2013.01); *G06K 7/0008* (2013.01); *H01Q 1/2208* (2013.01); *G06K 19/07749* (2013.01); *G06K 7/10366* (2013.01); *A61B 5/04085* (2013.01); *A61B 2562/08* (2013.01); *A61B 5/04286* (2013.01)
USPC ..................... 340/10.1; 340/572.1; 340/572.7

(58) Field of Classification Search
USPC ............ 340/10.1, 572.1, 572.7, 572.8, 573.1, 340/5.82, 10.32, 10.342; 600/300; 128/903
See application file for complete search history.

(56) References Cited

U.S. PATENT DOCUMENTS 6,298,255 B1   10/2001  Cordero et al.
6,934,570 B2   8/2005  Kiani et al.
(Continued)

FOREIGN PATENT DOCUMENTS

JP   2006268279 A   10/2006
WO   2004079647 A   9/2004

OTHER PUBLICATIONS

International Search Report issued for PCT/US07/081241, dated May 30, 2008, 3 pages.

(Continued)

*Primary Examiner* — Toan N Pham
(74) *Attorney, Agent, or Firm* — Shvarts & Leiz LLP

(57) ABSTRACT

This invention relates to a physiological sensor which acquires pre-programmed data from an electrode or an electrode array using Radio Frequency Identification (RFID) technology. The source of the sensor may be authenticated by means of a wireless interface between an RFID transponder affixed to the electrode array, and an RFID interrogator embedded in the patient interface cable. The criteria for use are then verified to ensure that they are met by the electrode array before beginning signal acquisition. If the criteria are not met, a message is provided to the user via the monitor.

20 Claims, 5 Drawing Sheets

(51) Int. Cl.
  *G06K 7/00*      (2006.01)
  *G08C 17/02*     (2006.01)
  *H01Q 1/22*      (2006.01)
  *G06K 19/077*    (2006.01)
  *G06K 7/10*      (2006.01)
  *A61B 5/0408*    (2006.01)
  *A61B 5/0428*    (2006.01)

(56) References Cited

U.S. PATENT DOCUMENTS

| | | |
|---|---|---|
| 7,277,677 B2 | 10/2007 | Ida et al. |
| 7,733,218 B2 | 6/2010 | Drago et al. |
| 7,901,394 B2 | 3/2011 | Ireland et al. |
| 8,427,321 B2 * | 4/2013 | Brumer et al. ............. 340/572.1 |
| 2004/0008123 A1 | 1/2004 | Carrender et al. |
| 2004/0225199 A1 | 11/2004 | Evanyk et al. |
| 2005/0258242 A1 | 11/2005 | Zarembo |
| 2005/0289083 A1 | 12/2005 | Ngai et al. |
| 2006/0061475 A1 | 3/2006 | Moskowitz et al. |
| 2007/0046471 A1 | 3/2007 | Nyalamadugu |

OTHER PUBLICATIONS

International Search Report issued for PCT/US07/081249, dated May 28, 2008, 4 pages.

* cited by examiner

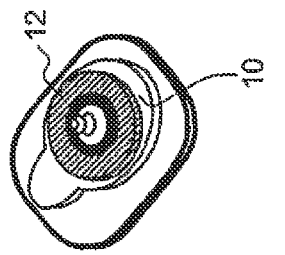
FIGURE 2b
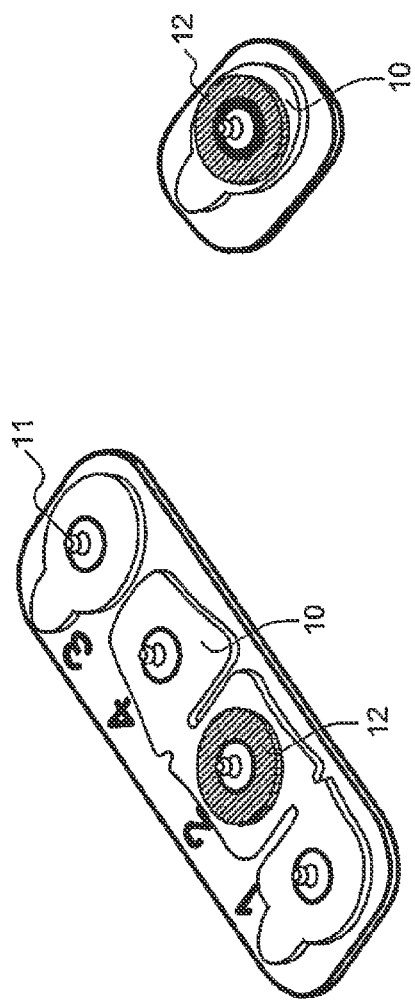
FIGURE 2a
FIGURE 2
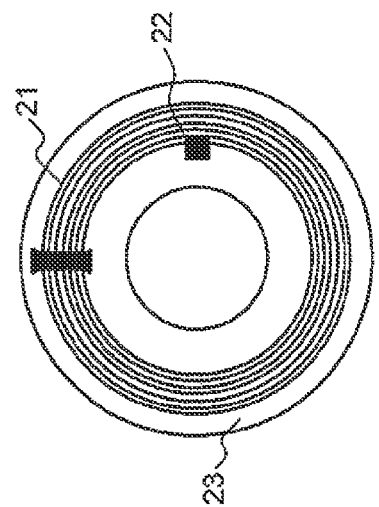
FIGURE 3

PHYSIOLOGICAL SENSOR SYSTEM WITH AUTOMATIC AUTHENTICATION AND VALIDATION BY MEANS OF A RADIO FREQUENCY IDENTIFICATION PROTOCOL WITH AN INTEGRATED RFID INTERROGATOR SYSTEM

CROSS-REFERENCE SECTION

This application is a continuation of U.S. patent application Ser. No. 13/315,486, filed Dec. 9, 2011, which is a continuation of U.S. patent application Ser. No. 11/871,585, filed Oct. 12, 2007, (now U.S. Pat. No. 8,077,039), which claims priority to U.S. Provisional Application No. 60/851,437, filed Oct. 13, 2006, all of which are incorporated herein by reference in their entireties.

BACKGROUND OF THE INVENTION

RFID technology-based wireless transmission of data enables effective communication of data and data management in the absence of physical connections, with a transmission quality that is equal to contact-based technologies. One such application is the use of RFID technology as an alternate to contact smart cards, or other memory devices that require contact in order to communicate their stored data.

When acquiring physiological signals for recording and analysis via biomedical sensors, it is valuable to the user that certain information about the sensor be available to the monitoring system. This information may include type of sensor, configuration of electrodes, the number of times the sensor has been used, date of manufacture of the sensor, identity of the manufacturer and the manufacturing lot number. The monitor can utilize this information to determine how to process data or even to detect whether to allow use or to limit reuse of the sensor. An alternative to entering the data manually is to include such data in a memory device integrated into the sensor itself. Integration of memory devices in biomedical sensors and in medical devices in general has been documented in conjunction with numerous previous inventions. Perhaps the most representative is U.S. Pat. No. 6,298,255. In U.S. Pat. No. 6,298,255 Cordero et al. describe a sensor system including a monitor, a smart sensor and the accompanying hardware and software interface to authenticate the source and validity of the sensor. A smart card memory module is incorporated into an electrophysiological sensor for the purpose of storing data pertaining to the sensor. The memory module is mounted on a rigid connector used to connect the sensor to the monitor. Although the data contained in the memory device for the present invention may be the same as that described in U.S. Pat. No. 6,298,255, the nature of the memory device and the method by which the system communicates with the memory device are distinct.

In US Patent Application 2004/0008123A1 Carrender et al. focuses on the use of RFID for monitoring and tracking medical devices utilizing RFID techniques. An RFID tag programmed with information about the manufacturing of the device as well as the status of the device, is attached to the medical device to be monitored. A detection system is coupled to the tag in order to access the data. In an alternate arrangement the data can be read and revised by a reader device which may be linked to a database.

US Patent Application US2005/025842A1 Zarembo describes a system and a method for managing information related to implantable medical devices. The system is comprises a disposable RFID unit external to the implantable medical device (IMD) yet packaged with the device. The RFID unit contains information primarily related to the manufacturing of the device. Such data may include inventory information, assembly management information, measurement results, and traceability information. An RF communication device is used to interrogate the RFID unit. This RF communication device may be associated with the IMD programmer or it may be part of a global or hospital communication network.

One further RFID application in the medical field is protection against counterfeiting of pharmaceutical and medical devices. In US Patent Application US 2005/0289083 Ngai et al. detail a system that employs a parent-child relationship between two RFID tags for the purpose of authenticating products that are delivered in a plurality of containers packaged within a single package. Each container is affixed with an RFID child tag and the outer package is affixed with a parent tag. Using various methodologies based on the data stored in each tag (e.g. a UID) and on information in a database, the authenticity of the relationship and that authenticity of the package is determined.

SUMMARY OF THE INVENTION

The invention relates to the use of a wireless communication technology, namely RFID, to enable the task of authentication and validation of an electrode array by a sensing patient interface cable. It also comprises the means by which an electrode, electrode array or physiological measuring device, bearing a passive RFID transponder, or tag, may be detected and may provide stored data to a RFID interrogator and then to an associated physiological monitoring system. The data may include the manufacturer, information about the manufacturing history and the use history of the electrode array for the purposes of authenticating the electrode array source and verifying that the electrode array meets the criteria for use (e.g. before expiration date, number of previous uses, etc.). Data that relate to calibration may also be programmed.

This function is performed with the components of the interrogator system, including an interrogator integrated circuit (IC), microprocessor, antenna and antenna matching circuits located within a flexible patient interface cable that connects the electrode array to the monitoring system. The entire system also performs this function with limited power consumption in order to be retrofittable to an existing non-RFID-based sensor-to-monitor interface. The invention of the current application is designed to be compatible with monitoring systems using the smart memory device-based system of the type shown in U.S. Pat. No. 6,298,255. Therefore, it must meet all the requirements of the device described in that patent including power consumption limits and output data structure as the data is expected in smart memory module format, ISO 7816. When the sensor is used to acquire signals, i.e. when the patient interface cable and the electrode array are mated through connection of the snaps to the snap sockets, the pair of RFID antennae has no more than 15 mm of separation. This read distance is shorter than typical application. Consequently, the power consumption can be reduced and the reliability is increased. However additional measures in the interrogator system circuitry are required to further control and limit the power consumption.

Electrophysiological data is transmitted from the contact surface or surfaces of the electrode(s) to the physiological monitor by direct contact between conductive snaps on the electrode array and snap sockets embedded in the patient interface cable. When the snaps are mated the transponder which is located on the sensor is detected. In this invention, there is no need for a network of RFID interrogator locations, or even the need to carry around a handheld interrogator due to the fact that the interrogator is integrated into a cable system which would otherwise be required to transmit the electrophysiological signal to the biopotential monitor.

When the electrode array with its affixed transponder is brought within the field generated by the interrogator, there is a measurable voltage change. This voltage change can be used as a means to detect the presence of the transponder. The presence of the transponder may also be identified by successful interrogation and response of the transponder. Once the transponder is detected, the two components can communicate via modulation of the RF electric field generated by the antennae.

Upon detection of the RFID transponder, the interrogator prompts the transponder IC for its stored data. The data is then converted by the microprocessor, to the memory format in ISO7816 that is expected by the legacy monitoring system. In an alternate embodiment, the data may first need to be decrypted prior to conversion as an added element of security. The information is then processed as described in U.S. Pat. No. 6,298,255.

In a hospital setting, this physiological sensor may frequently be used in the presence of electrosurgical units which are potentially a significant source of interference in the communication between the interrogator and the transponder. Therefore extra measures are taken in this sensor design to reduce interference from electrosurgical units (ESU) which are frequently encountered in a hospital setting. To decrease ESU interference, filtering is added to the patient interface cable.

This implementation of wireless technology may be further advantageous in a context in which a physiological sensor does not form a mechanical connection with the monitor but rather the acquired signals are also transmitted by a wireless technology.

BRIEF DESCRIPTION OF FIGURES

FIG. 2a is a perspective view of a multi-electrode embodiment of an electrode array with a mounted RFID transponder.

FIG. 2b is a perspective view of a single-electrode embodiment of an electrode array with a mounted RFID transponder.

FIG. 3 is a drawing of a sample RFID transponder for this application (HF)

DETAILED DESCRIPTION OF PREFERRED EMBODIMENTS

Figure 1:
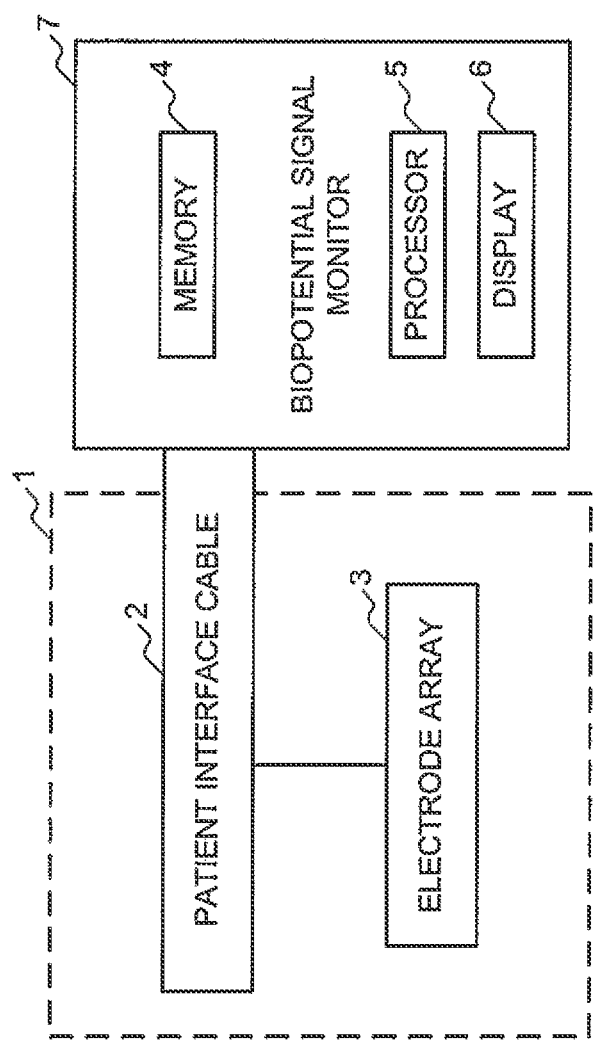
FIG. 1 is a block diagram illustrating the components of the Electrophysiological Sensor System

The invention consists of an electrophysiological sensor 1 (FIG. 1), comprised of an electrode array 3 used for acquiring physiological signals from a patient and an interface cable 2 which connects to the electrode array 3. This sensor is typically connected to a biopotential signal monitor 7 that contains memory storage 4, a processor 5 and a display device 6 which are used to store, analyze and display the physiological signals to a user.

Electrophysiological data is transmitted from the contact surface or surfaces of the electrode 10 or electrodes (shown in FIGS. 2a & 2b) to the monitor 7 (not shown) by the typical method of direct contact between conductive snaps 11 on the electrode array and snap sockets 30 (referring to the top half of a snap connector) embedded in the interface cable. The electrode array, which adheres to the patient's skin consists of at least one electrophysiological electrode 10, preferably constructed of silver/silver chloride. An RFID transponder 12 is adhesively affixed to the electrode array.

An RFID transponder 12 is comprised of an antenna 21 and a transponder integrated circuit (IC) 22 (FIG. 3). The microchip 22 on the RFID transponder 12 is a memory device that is programmed by the biomedical sensor manufacturer with data regarding the history and status of the electrode array. In this embodiment, the RFID transponder 12 is constructed on a flexible substrate 23, preferably polyester or polypropylene. It has a coil antenna 21 preferably formed of etched or deposited copper, but may also be aluminum. The RFID transponder IC 22 has adequate EEPROM memory capacity of to store any required data. Alternately, the memory may be EPROM or PROM (programmable read-only memory). Preferably the transponder IC 22 has a memory capacity of 256-512 bytes. One such IC is the NXP SLIS3001 (I-CODE1)(NXP Semiconductors Netherlands B. V., Eindhoven, The Netherlands). The RFID transponder 12 is passive which means that it contains no battery and draws its power from the host system via the interrogator antenna (not shown). The transponder resonates in the High Frequency (HF) band (~13.56 MHz)

The transponder 12 has adhesive backing and is formed in the shape of an annular ring, no more than 1.5 inches (38 mm) in diameter. This is in line with commercially available RFID transponders. The transponder is affixed to the electrode array with the antenna and the IC on the surface that contacts the electrode, thus aiding in protecting the electronics from damage due to exposure to liquid or improper handling. It is positioned around a male EKG electrode-type post or "snap" 11 on one electrode in the array. In alternate embodiments, the transponder could be of any shape or design that would enable it to be mounted on the electrode array. In an alternate embodiment still, multiple transponders may be placed on multiple electrodes in the array.

Upon connection of the electrode array 3 to the patient interface cable 2, both electrophysiological data and data relating to the electrode array are transmitted to the biopotential signal monitor (not shown). Electrophysiological data is transmitted via the snaps while electrode array data stored on the transponder IC such as data pertaining to authentication, manufacturing information and validity of the electrode array, are transmitted by radio frequency transmission (RF).

The patient interface cable 2 (FIGS. 4a & 4b) has a connector 39 at one end that mates with the biopotential signal monitor. At the opposing end, the cable has multiple embedded EKG electrode-type sockets 30 designed to attach to the snap in the center of each electrode in the electrode array. There are an equivalent number of sockets in the cable as there are electrodes in the array. There may be as few as one socket in the cable. The EKG electrode-type sockets 30 are electrically connected by a series of conductive wires 31. In an alternate embodiment the sockets are mounted in fixed positions in a flexible circuit board with conductive traces to from the cable and to conduct signal from each electrode of the array via the snap socket to the monitor. In yet another embodiment the transmission lines are conductive traces which are constructed of a conductive ink, such as silver/silver chloride (Ag/AgCl) printed on a flexible substrate on the substrate of the flexible circuit board.

The patient interface cable housing the EKG electrode-type sockets and conductive transmission lines is over-molded 38 with a thermoplastic elastomeric material. Only the bottom surface of the snap socket is exposed for attachment to the electrode array 3. This assists in protecting the circuit and the contacts from the harsh environment of an operating room, reduces the likelihood of liquid ingress and also creates a flexible interface for easy use by clinicians and for patient fit.

The patient interface cable 2 also houses an RFID interrogator system. The interrogator system is comprised of an interrogator IC, the antenna for the interrogator 32, and 2 matching circuits. The interrogator IC may have an integrated microprocessor for preliminary processing of the data.

In the preferred embodiment, the interrogator system is contained on two printed circuit boards (PCBs) embedded in the cable—the Tail PCB 40 and the Head PCB 33. The interrogator IC may be the MLX90121 (Melexis) chip or a similar commercially available chip that operates in the HF frequency band (13.56 MHz). The RFID interrogator IC may be capable of communicating with microchips compliant with any of various ISO contactless integrated circuit proximity and vicinity card protocols, e.g. ISO 14443A/B, ISO 15693.

In this embodiment, the interrogator antenna is located on the Head PCB 33 while the interrogator IC is located on the Tail PCB 40. Components for power management and to reduce interference may also be mounted on this Tail PCB 40. Additionally, the Tail PCB may also contain a relatively narrow band passive filter centered around 13.56 MHz to receive the input of the MLX90121, or equivalent interrogator IC. The external filter keeps the ESU interference from exceeding the input voltage capacity of the MLX90121.

For power management, in the preferred embodiment, a switching power supply is used to limit the voltage to the Power Amplifier of the MLX90121 rather than a standard current limiting circuit which uses power less efficiently. In another embodiment, the power limitation is overcome by using a bank of capacitors on the Tail PCB. Capacitors can be charged at a slow rate and draw the charge out of them at a high rate. A 10 mF capacitor bank can be charged up to 5 volts with a 1 ma charge current over a period of 1 second and then it can be drawn at 10 ma for 0.1 second.

Figure 5:
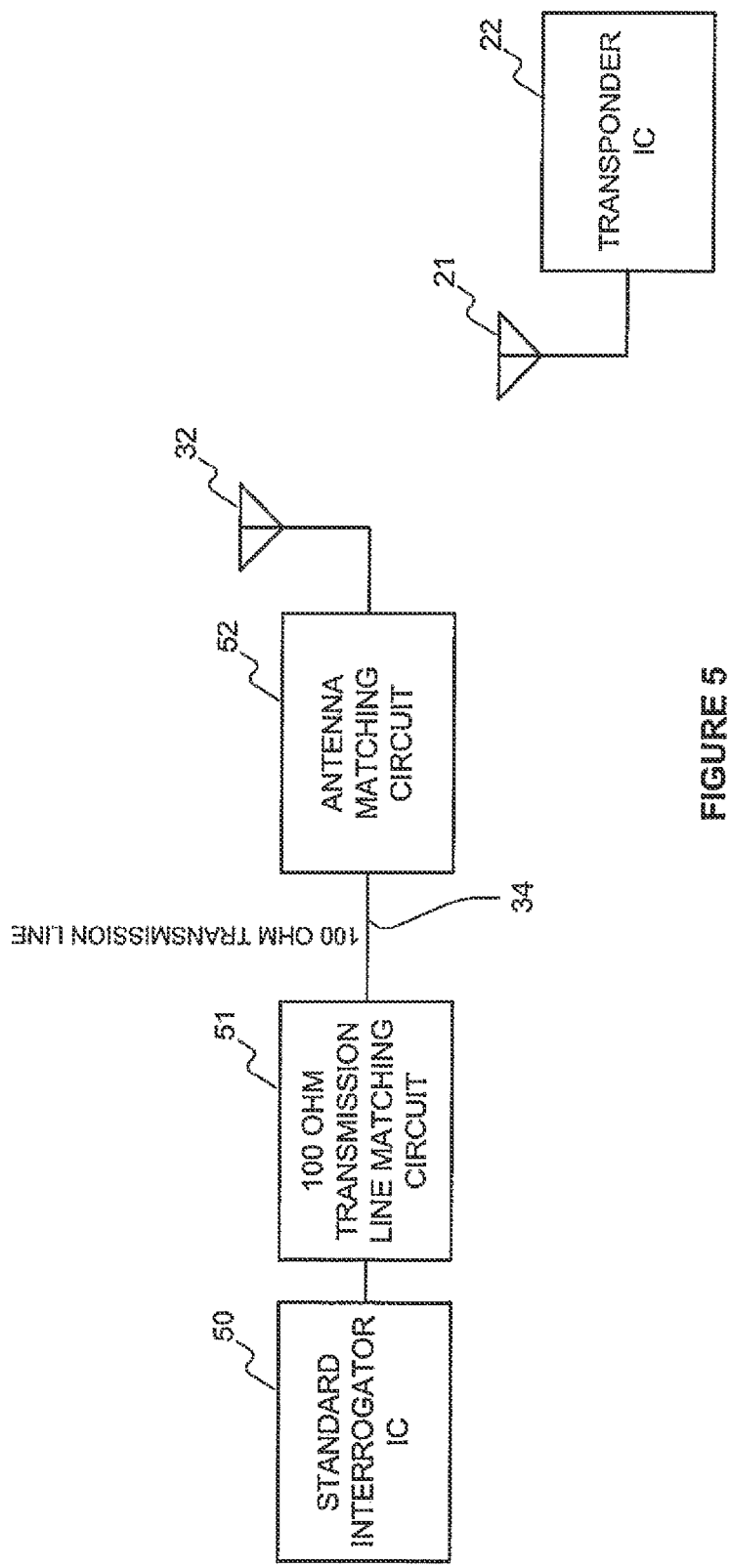
FIG. 5 is a block diagram of the relationship between the interrogator and the transponder.

In this preferred embodiment, the interrogator antenna 32 is etched on the Head PCB 33. Two conductive wires, specified as a 100 ohm twisted pair 34 are connected at one end to the Head PCB 33 and at the other end, to the Tail PCB 40. Such conductive wires transmit AC signal to the Head PCB thus providing power to the interrogator antenna 32. As illustrated in FIG. 5, attached to the interrogator IC 50 is an impedance matching circuit 51 that matches the output impedance of the interrogator IC 50 to the 100 ohm twisted pair transmission line 34. Transmission lines of other impedances (e.g. 50 ohm or 300 ohm) may also be used. At the far end of the transmission line is a matching circuit 52 and an antenna 32. The matching circuit 52 matches the impedance of the transmission line 34 to the impedance of the antenna 32 and forms a resonant circuit with the antenna. This matching circuit may also include a resistor to lower the Q of the resonant circuit to increase the bandwidth of the circuit. The interrogator antenna 32 generates an RF electric field with the transponder antenna 21 enabling communication with the transponder IC 22.

Figure 4A:
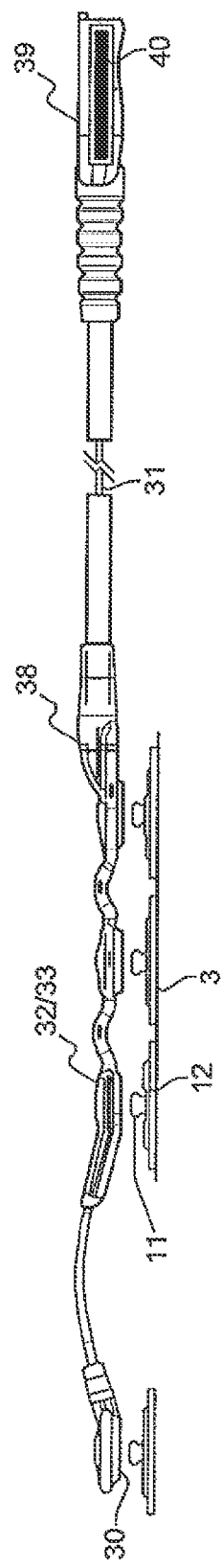
FIG. 4a is a side view of the complete patient interface cable and its relationship to the biomedical sensor for electrophysiological signal acquisition.
Figure 4B:
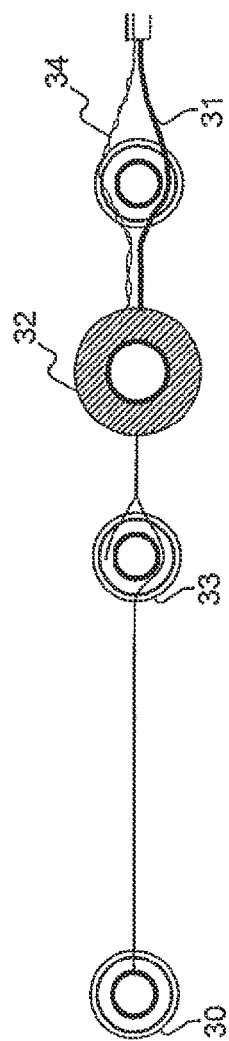
FIG. 4b is a top view of an unmolded patient interface cable showing the wiring and integrated hardware.

The placement of this Head PCB 33 is around or alternately beside a snap socket in the location corresponding to the affixed transponder on the electrode array. The Head PCB is held in place by a solder connection to the snap. Alternately it may be held in place by a thermoplastic over-mold (or pre-mold). The Head PCB may share the same flexible substrate as the conductive traces and/or may be a combination of a flexible and a rigid circuit board to increase strength and reliability. The interrogator antenna 32 has a maximum diameter of 30 mm. The interrogator antenna 32 on the Head PCB 33 is placed such that when the cable and electrode array are mated, the antenna is positioned directly above and parallel to the RFID transponder 12 affixed to the electrode array, as illustrated in FIG. 4a. In the preferred embodiment, the tail PCB 40 is integrated into the connector 39 that mates with the biopotential signal monitor.

In one embodiment, the interrogator antenna and interrogator IC are co-located on the Head PCB. The matching circuits are then modified to accommodate the change in relative position between the interrogator antenna and the interrogator IC. In yet another embodiment, the Tail PCB 40 containing the circuitry including an interrogator IC, a microprocessor, and electronics and for matching the interrogator antenna may be housed in an independent enclosure or be integrated into the monitor hardware.

In this application, when the electrode array 3 is mechanically attached to the patient interface cable 2, by the conductive snaps 11 mated to snap sockets 30, and the interrogator antenna 32 and the RFID transponder 12 are consequently in proximity to the other, the preferred distance between the interrogator antenna and the transponder when the cable is connected to the electrode array is 2-15 mm.

When the transponder IC is brought within the field generated by the interrogator, a measurable voltage change is observed at the output of the antenna matching circuit 52. Detection of this voltage change is used as a means to detect the presence of the transponder. In one embodiment, the interrogator system continuously checks via continuous polling for a change in voltage by way of an analog-to-digital converter that is constantly sampling the voltage. An alternate embodiment would use a hardware voltage comparator to sense the change in voltage. This voltage change can be used as a means to detect the presence of the transponder. An alternate means of transponder detection is to simply interrogate the device and determine if there is any response.

These detection methods also enable the interrogator system to detect the absence, or removal of the transponder from the detection field. Thus, the biopotential monitoring system knows when the electrode array is and is not connected to the patient interface cable. Once the transponder is detected, the two components can communicate via RF modulation as per standard RFID communication methods.

Figure 6:
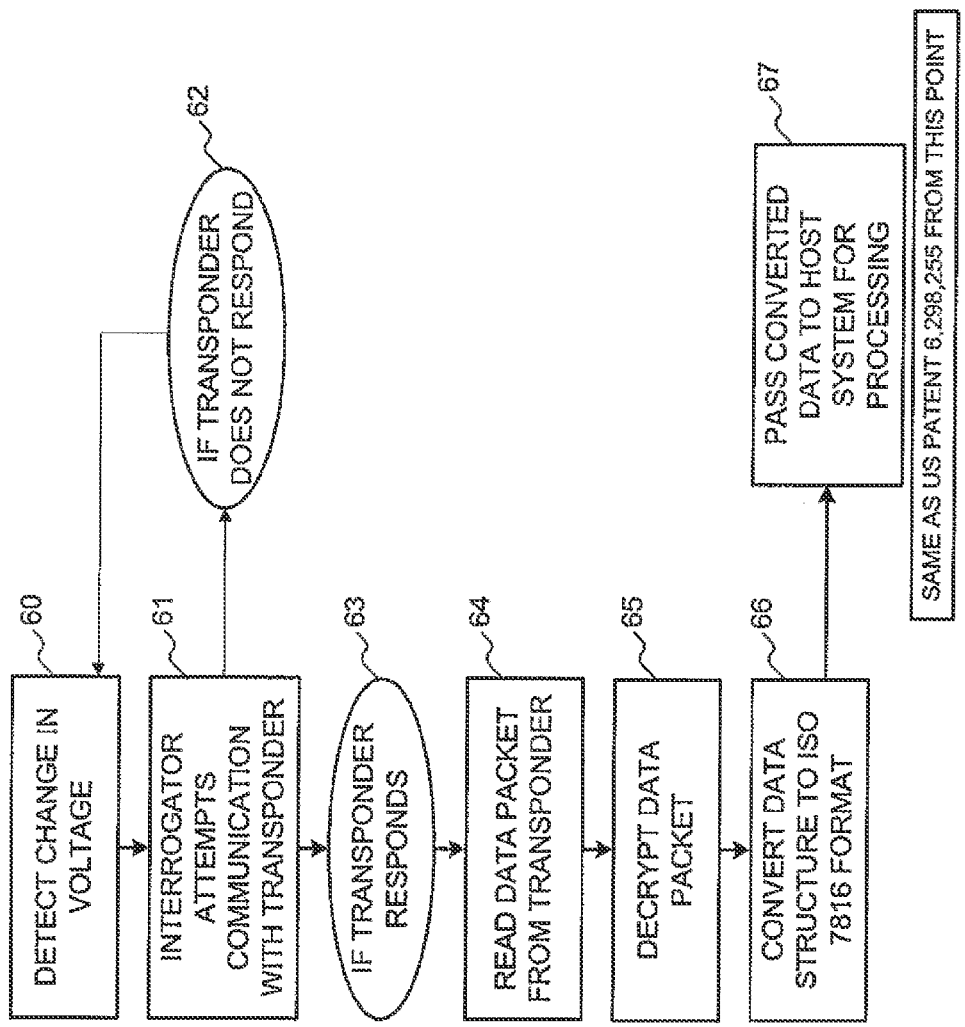
FIG. 6 is a flow chart of the detection and communication during the interrogation process.

FIG. 6 outlines the high-level steps for detection and communication. The system detects a change in voltage 60 and then proceeds to interrogate the transponder IC 61. If the transponder does not respond to interrogation by the interrogator 62, the state of the system returns back to trying to detect a voltage change 60. If the transponder does respond to interrogation by the interrogator 63, the interrogator proceeds to read the data packet stored on the transponder IC 64 contained by the transponder. Then the data packet is decrypted by the microprocessor if the data was previously encrypted 65 and the structure of the data is converted to ISO7816 format to emulate a smart module 66, which is what is expected by the legacy host system. Once the data is converted, it is passed on to the biopotential signal monitor for further processing 67—primarily authentication and validation of the sensor. The authentication and validation aspects of this system are described in detail in U.S. Pat. No. 6,298,255. Additionally, the data packet may be revised, possibly to reflect a change in sensor status, for example incrementing a usage counter, and then written to the transponder IC.

Various data concerning the origin and manufacture of the electrode array are stored in the transponder IC. This data includes but is not limited to a key code, a manufacturer code, an OEM code, a product shelf life code, an electrode type code, the lot code and serial number and the usage count. All or a part of the data are stored in encrypted form with a single or multiple layered encryption. The data may also include a digital signature that may be used to authenticate and validate the electrode array in the manner taught by U.S. Pat. No. 6,298,255. The manufacturer code is used to authenticate the source of the electrode array, while the product shelf-life code, the usage count and the sensor type code are used to determine whether the sensor meets the necessary criteria for use. Calibration data relating to the electrode array may also be stored in the transponder IC, allowing avoidance of recalibration if the sensor is disconnected and reconnected to a different monitor. This is commonly done in medical or hospital settings in conjunction with patient transport.

In an alternate embodiment, where the restrictions imposed by the legacy system are not applied, methods and components relating to the power limiting circuitry and to the conversion of the data to contact based ISO7816 data structure are not incorporated.

In an alternative embodiment, the RFID transponder is embedded into an optoelectrical device for obtaining biological signals. These devices contain no direct contact with the patient, so the RFID transponder is a convenient way to keep the device from having any external contacts such as the ones on a contact smart chip.

The incorporation of RFID-based technology into an electrophysiological monitoring system provides several important and significant advantages, both technical and economic. The wide-spread and ever increasing acceptance and demand for RFID tagging (i.e. affixing an RFID transponder on any item) in a number of industries has driven the cost of RFID microchips to much less than that of non-RFID semiconductor memory devices of similar capability and capacity. In addition, implementing RFID as an alternative to contact smart chips requires fewer electrical connections to the sensor. This provides a lower manufacturing cost due to the reduction in the required number of conductive traces and contact pads on both the sensor side and the monitor side of their connection. The lack of contact connections and the absence of the associated connection pads and conductors also provide increased reliability by avoiding device failures caused by poor contact impedances and the likelihood of a communication malfunction due to the ingress of fluids such as water or body fluids into the space between adjacent contact pads. This implementation of wireless technology may also be advantageous in a context in which the biomedical sensor does not form a mechanical connection with the monitor but rather the acquired signals are also transmitted by a wireless technology. In such a context, this invention has important advantages for maintaining device sterility.

While the foregoing invention has been described with reference to its preferred embodiments, various alterations and modifications will occur to those skilled in the art. All such alterations and modifications are intended to fall within the scope of the appended claims.

What is claimed is:

1. A method for communicating data, comprising:
   receiving physiological data from a physiological sensor, the physiological data transmitted by a first transmission technique;
   interrogating an RFID transponder using an RFID interrogator, wherein the interrogating causes the RFID transponder to transmit non-physiological data by a second transmission technique; and
   receiving the non-physiological data using an RFID antenna coupled to an RFID antenna matching circuit.

2. The method of claim 1, wherein the first transmission technique is a wired technique.

3. The method of claim 1, wherein the second transmission technique is a wireless RFID technique.

4. The method of claim 1, further comprising displaying the physiological data using a monitor.

5. The method of claim 4, wherein displaying the physiological data comprises displaying the physiological data only if the non-physiological data meets a predetermined criteria.

6. The method of claim 1, wherein receiving the non-physiological data comprises receiving an encrypted data packet stored on the RFID transponder.

7. The method of claim 1, wherein the non-physiological data is selected from the group consisting of a number of times the sensor has been used, a sensor type code, calibration data, and any combination thereof.

8. The method of claim 1, further comprising detecting the presence of the RFID transponder in a detection field using the RFID interrogator.

9. The method of claim 1, wherein the physiological data comprises EKG data.

10. The method of claim 1, further comprising providing power to the RFID transponder via the RFID antenna.

11. A method for communicating data, comprising:
    receiving physiological data transmitted by a first transmission technique, wherein the physiological data is from a physiological sensor; and
    receiving non-physiological data transmitted by a second transmission technique from an RFID transponder, wherein the RFID transponder comprises a memory device.

12. The method of claim 11, wherein the first transmission technique is a wired technique.

13. The method of claim 11, wherein the second transmission technique is a wireless RFID technique.

14. The method of claim 11, further comprising displaying the physiological data using a monitor.

15. The method of claim 14, wherein displaying the physiological data comprises displaying the physiological data only if the non-physiological data meets a predetermined criteria.

16. The method of claim 11, wherein receiving the non-physiological data comprises receiving an encrypted data packet stored on the RFID transponder.

17. The method of claim 11, wherein the non-physiological data is selected from the group consisting of a number of times the sensor has been used, a sensor type code, calibration data, and any combination thereof.

18. The method of claim 11, further comprising detecting the presence of the RFID transponder in a detection field using the RFID interrogator.

19. The method of claim 11, wherein the physiological data comprises EKG data.

20. The method of claim 11, further comprising providing power to the RFID transponder via the RFID antenna.

* * * * *